US00PP13199P2

(12) United States Plant Patent
Cain

(10) Patent No.: US PP13,199 P2
(45) Date of Patent: Nov. 12, 2002

(54) GRAPEVINE CV. 'SUGRASEVENTEEN'

(76) Inventor: David W. Cain, 6713 Mellon Ct., Bakersfield, CA (US) 93380

( * ) Notice: Subject to any disclaimer, the term of this patent is extended or adjusted under 35 U.S.C. 154(b) by 1 day.

(21) Appl. No.: 09/770,524

(22) Filed: Jan. 25, 2001

(51) Int. Cl.[7] ..... A01H 5/00
(52) U.S. Cl. ..... Plt./205
(58) Field of Search ..... Plt./205

(56) References Cited

U.S. PATENT DOCUMENTS

PP8,297 P 7/1993 Olmo ..... Plt./47.1

*Primary Examiner*—Bruce R. Campell
*Assistant Examiner*—Michelle Kizilkaya
(74) *Attorney, Agent, or Firm*—Knobbe, Martens, Olson & Bear

(57) ABSTRACT

A new and distinct grapevine variety characterized by firm, medium-sized red berries that ripen very late and are able to tolerate rainfall or adverse weather conditions better than other available late red seedless varieties.

1 Drawing Sheet

BACKGROUND AND SUMMARY OF THE INVENTION

This invention relates to the discovery and asexual propagation of a new variety of grapevine, *Vitis vinifera* cv. 'Sugraseventeen'. The new variety was first hybridized by David W. Cain in Wasco, Kern County, Calif., the variety being originated by controlled hybridization and subsequent ovule culture of normally abortive seeds. The new variety is characterized by producing medium firm red seedless berries of medium size which ripen very late. The new variety tolerates rain and adverse weather conditions better than other available late red seedless varieties.

The seed parent is the (unpatented) 'Emperor' variety and the pollen parent is the (unpatented) 'Ruby Seedless' variety. The parent varieties were first crossed in May, 1987, with the date of first flowering being May, 1990. The new 'Sugraseventeen' variety was first asexually propagated by David W. Cain in December, 1990 in Wasco, Kern County, Calif., using dormant cuttings.

The new grapevine variety cv. 'Sugraseventeen' resembles its seed parent the 'Emperor' variety, in that it produces late ripening red berries which tolerate rain and adverse weather. It differs from the 'Emperor' variety in that the berries contain abortive seed remnants which are tiny and softer than seeds of the 'Emperor' variety. It differs from the pollen parent, the 'Ruby Seedless' variety by producing more rounded berries that ripen later.

'Sugraseventeen' is distinguished from other commonly grown red seedless grapes such as the 'Crimson Seedless' variety (nonpatented) and the '3-14-71' variety (U.S. Plant Pat. No. 8,297). 'Sugraseventeen' is distinguished from the Crimson Seedless variety by producing more rounded, softer berries in larger clusters which are more rain tolerant.

'Sugraseventeen' differs from the '3-14-71' variety by producing rounder, softer berries. 'Sugraseventeen' clusters are also larger, averaging 728 grams as compared to 446 grams in the '3-14-17' variety. Additionally, the young shoots of 'Sugraseventeen' are more pubescent than the young shoots of the '3-14-17' variety.

The new 'Sugraseventeen' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
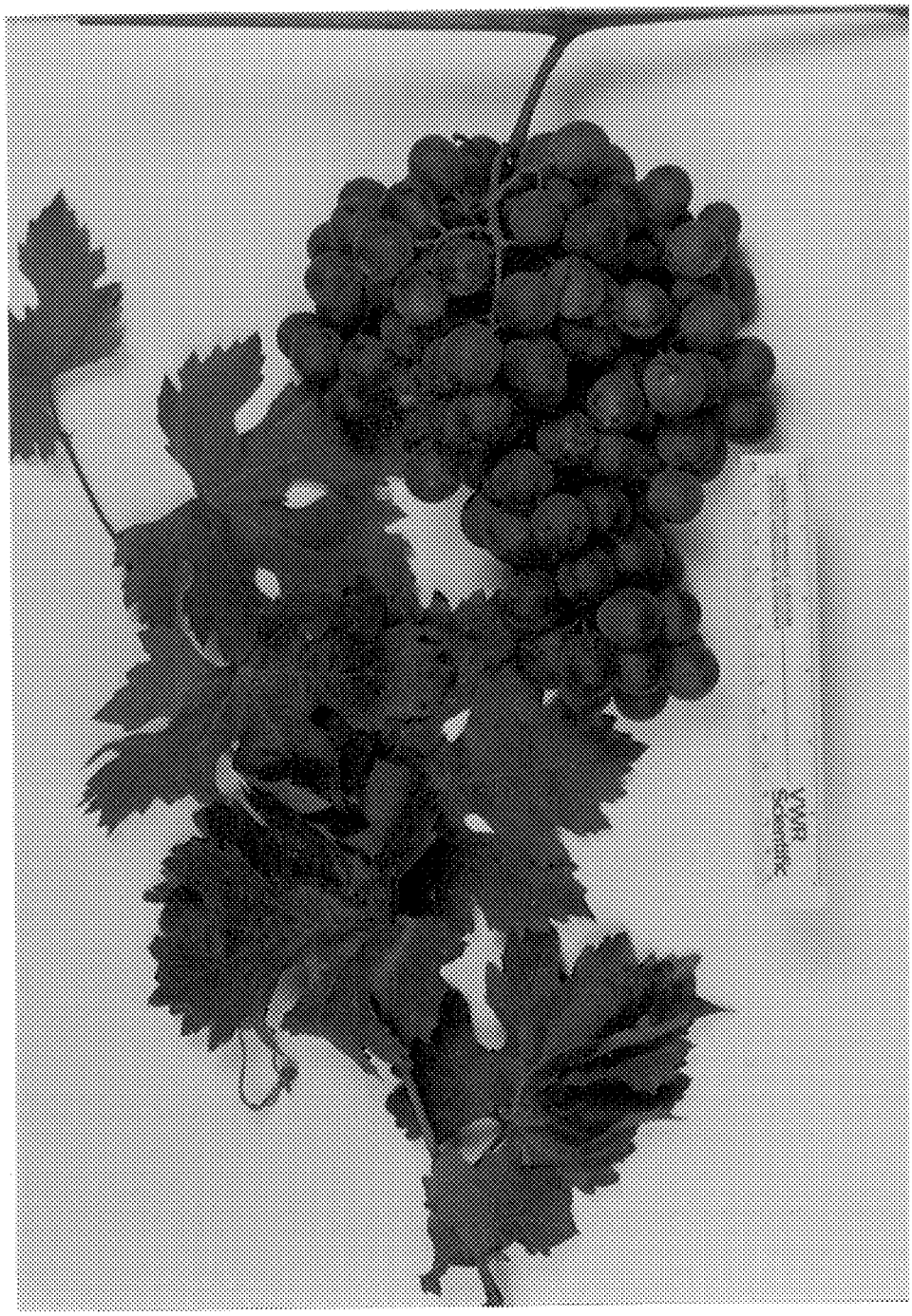

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugraseventeen' plants grown in the vicinity of Wasco, Kern County, Calif., during 1999–2000, and is believed to apply to plants of the variety grown under similar conditions of soil and climate elsewhere:

VINE

General:
- *Size*.—Very large.
- *Vigor*.—Very vigorous.
- *Density of foliage*.—Dense.
- *Productivity*.—Medium productive.
- *Root stock*.—Own.

Trunk:
- *Shape*.—Very stocky.
- *Straps*.—Very long and wide.
- *Surface texture*.—Medium-shaggy.
- *Inner bark color*.—About 177A.

SHOOTS

Young shoot:
- *Form of tip*.—Half-open.
- *Distribution of anthocyanin coloration of tip*.—Piping (striped).

*Intensity of anthocyanin coloration of tip.*—Strong.
*Density of prostrate hairs on tip.*—Very dense.
*Density of erect hairs on tip.*—Absent.

Flowering shoot:
*Vigor during flowering.*—Very strong.
*Attitude during flowering on shoots which are not tied.*—Drooping.
*Color of dorsal side of internodes.*—About Red 183A.
*Color of ventral side of internodes.*—About Green 144A with red stripes.
*Color of dorsal side of nodes.*—About Green 144A with red stripes.
*Color of ventral side of nodes.*—About Red 183A.
*Density of erect hairs on nodes.*—None.
*Erect hairs on internode.*—Absent.
*Density of prostrate hairs on nodes.*—Very sparse.
*Density of prostrate hairs on internodes.*—Medium.
*Anthocyanin coloration of buds.*—Absent or very weak.

Tendrils:
*Distribution on the shoot at full flowering.*—Discontinuous.
*Thickness.*—Medium.
*Color.*—About Yellow-Green 144B.
*Form.*—Trifurcated.
*Number of consecutive tendrils.*—Three or more.
*Length of tendril.*—Very long, about 42.6 cm.

LEAVES

Young leaves:
*Color of upper surface of first 4 distal unfolded leaves.*—Reddish, about 183B Greyed-Purple group.
*Average intensity of anthocyanin coloration of six distal leaves prior to flowering.*—Strong.
*Density of prostrate hairs between veins at lower surface of 4th distal unfolded leaf.*—Very dense.
*Density of erect hairs between veins at lower surface of 4th distal unfolded leaf.*—Absent.
*Density of prostrate hairs on veins at lower surface of 4th distal unfolded leaf.*—Very dense.
*Density of erect hairs on veins at lower surface of 4th distal unfolded leaf.*—Absent.

Mature leaves:
*Average length.*—About 20.0 cm.
*Average width.*—About 23.2 cm.
*Size of blade.*—Very large.
*Shape of blade.*—Pentagonal.
*Number of lobes.*—7.
*Anthocyanin coloration of main veins on the upper side of the blade.*—Strong.
*Mature leaf profile.*—Involute.
*Blistering surface of blade upper surface.*—Very strong.
*Leaf blade tip.*—In the plane of the leaf.
*Undulation of margin.*—Pronounced.
*Apex.*—Cuspidate.
*Thickness.*—Thick.
*Undulation of blade between main and lateral veins.*—Overall.
*Shape of teeth.*—Both sides convex.
*Length of teeth.*—Short.
*Ratio length/width of teeth.*—Small.
*General shape of petiole sinus.*—Slightly open.
*Tooth at petiole sinus.*—Absent.
*Petiole sinus limited by veins.*—Absent.
*Shape of upper lateral sinus.*—Lobes strongly overlapping.
*Depth of upper lateral sinus.*—Very deep.
*Density of prostrate hairs between veins on lower surface of blade.*—Very dense.
*Density of erect hairs between veins on lower surface of blade.*—Very dense.
*Density of prostrate hairs on main veins on lower surface of blade.*—Very dense.
*Density of erect hairs on main veins on lower surface of blade.*—Very dense.
*Density of prostrate hairs on main veins on upper surface of blade.*—Present.
*Autumn coloration of leaves.*—Yellow.

Upper surface:
*Color.*—About 137A.
*Surface texture.*—Rugose.
*Surface appearance.*—Semi-glossy.
*Goffering of blade.*—Present.

Lower surface:
*Color.*—About 148B.
*Anthocyanin coloration of main veins on lower leaf surface.*—Medium.
*Glossiness.*—Weak.
*Pubescence.*—Pubescent.
*Surface texture.*—Rugose.
*Surface appearance.*—Dull.

Petiole:
*Length of petiole.*—Medium, about 13.7 cm.
*Length of petiole compared to middle vein.*—Much shorter.
*Density of prostrate hairs on petiole.*—Sparse.
*Density of erect hairs on petiole.*—Medium.
*Shape of base of petiole sinus.*—V-shaped.

Woody shoot:
*Shape.*—Stocky.
*Internode length.*—Medium, about 127.7 mm.
*Width at node.*—About 20.8 mm.
*Cross section.*—Circular.
*Surface.*—Smooth.
*Main color.*—About reddish brown, 173B Greyed-Orange group.
*Lenticles.*—Absent.
*Density of erect hairs on nodes.*—None.
*Density of erect hairs on internodes.*—None.
*Growth of axillary shoots.*—Few but strong.

Buds:
*Shape.*—Slightly pointed.
*Size.*—Medium.
*Position.*—Markedly held out.
*Cane but fruitfulness.*—Medium and distal fruitful.
*Time of bud burst.*—Very late, approximately Mar. 23, 2000.

FLOWERS

General:
*Flower sex.*—Pistilate with upright stamens.
*Length of first inflorescence.*—Long, about 26.6 cm.
*Position of first flowering node.*—$4^{th}$.
*Number of inflorescences per shoot.*—Up to 1.
*Date of full bloom.*—May 7, 2000.
*Time of bloom.*—Very late.
*Size (diameter of fully open flower).*—Large.

FRUIT

General:
*Ripening period.*—Late; about 60 days after Thompson Seedless variety.

*Use*.—Fresh market.
*Keeping quality*.—Good.
*Resistance*.—Insects: medium (typical of *Vitis vinfera*). Diseases: medium (typical of *Vitis vinifera*).
*Shipping quality*.—Good.
*Date of first harvest*.—Oct. 1, 2000.
*Solids-sugar*.—Medium.
*Refractometer test*.—About 18.0° brix.
*Acid*.—Low, about 0.35 g/L tartaric acid.
*Juice pH*.—3.92.

Cluster:
*Bunch size* (*peduncle excluded*).—Large.
*Bunch length* (*peduncle excluded*).—Long, about 25.7 cm.
*Bunch width*.—About 17.2 cm.
*Bunch weight*.—High, averaging about 972 g.
*Bunch density*.—Medium.
*Number of berries*.—About 350.
*Form*.—Conical.

Peduncle:
*Length of peduncle*.—Medium, about 5.5 cm.
*Lignification of peduncle*.—Strong.
*Color*.—About 145A.

Berry:
*Size*.—Medium.
*Uniformity of size*.—Uniform.
*Berry weight*.—Low to medium, about 3.0 g.
*Shape*.—Round to obtuse ovate.
*Presence of seeds*.—Rudimentary, about 10.5 mg/seed fresh weight.
*Cross section*.—Circular.
*Dimensions*.—Longitudinal axis about 16.9 mm; horizontal axis about 17.4 mm.
*Skin color* (*without bloom*).—About Dark Red to Violet, 183C.
*Coloration of flesh*.—None.
*Juiciness of flesh*.—Slightly juicy.
*Berry firmness*.—Medium.
*Particular flavor*.—None.
*Bloom* (*culticular wax*).—Medium.
*Pedicel length*.—Intermediate, about 6.86 mm.
*Berry separation from pedicel*.—Difficult.
*Visibility of hilum*.—Unclear.

Skin:
*Thickness*.—Thick.
*Texture*.—Tough.
*Reticulation*.—Absent.
*Roughness*.—Absent.
*Tenacity*.—Tenacious to flesh.
*Tendency to crack*.—None.

What is claimed is:

1. A new and distinct variety of grapevine cv. 'Sugraseventeen' as herein illustrated and described.

* * * * *